(12) United States Patent
Mehier (10) Patent No.: US 7,736,334 B2
(45) Date of Patent: Jun. 15, 2010

(54) IMPLANTABLE TUBE FOR INJECTION PARTICULARLY OF HEAT TRANSFER FLUID INTO ALL OR PART OF A HUMAN OR ANIMAL TISSUE

(75) Inventor: Henri Mehier, Lyons (FR)

(73) Assignee: Centre d'Etude et de Recherche Medicale d'Archamps, Archamps (FR)

( * ) Notice: Subject to any disclaimer, the term of this patent is extended or adjusted under 35 U.S.C. 154(b) by 284 days.

(21) Appl. No.: 11/910,986

(22) PCT Filed: Mar. 13, 2006

(86) PCT No.: PCT/FR2006/050218

§ 371 (c)(1),
(2), (4) Date: Oct. 9, 2007

(87) PCT Pub. No.: WO2006/108974

PCT Pub. Date: Oct. 19, 2006

(65) Prior Publication Data

US 2008/0171982 A1 Jul. 17, 2008

(30) Foreign Application Priority Data

Apr. 12, 2005 (FR) .................................. 05 50936

(51) Int. Cl.
*A61F 7/12* (2006.01)
(52) U.S. Cl. ..................................................... 604/113
(58) Field of Classification Search ......... 604/113–114; 600/595, 520, 526, 549, 561, 505; 606/24, 606/27–28; 607/99, 113, 96, 98, 115, 116, 607/143
See application file for complete search history.

(56) References Cited

U.S. PATENT DOCUMENTS 1,995,302 A * 3/1935 Goldstein .................... 604/114
4,038,519 A * 7/1977 Foucras ....................... 392/472
5,492,529 A * 2/1996 Neuwirth et al. ............ 607/143

(Continued)

FOREIGN PATENT DOCUMENTS

FR 2790965 A1 9/2000

(Continued)

OTHER PUBLICATIONS

International search report for PCT/FR2006/050218, dated Jul. 11, 2006.

(Continued)

*Primary Examiner*—Manuel A Mendez
(74) *Attorney, Agent, or Firm*—Heslin Rothenberg Farley & Mesiti P.C.

(57) ABSTRACT

Implantable tube, for heating by conduction a heat transfer fluid for injection into all or part of a human or animal tissue, is provided with a wall having distal, median and proximal parts and comprising connecting elements for direct or indirect connection of the distal part to a fluid reservoir, and two means for connection to the terminals of an electric power supply, for incoming and outgoing current in the wall. The tube has a resistance less than $0.01\Omega$ in its median and proximal parts, and a resistance of between 0.2 and $2\Omega$ in its distal part. The median and proximal parts are connected electrically in series to the distal part; the tube having no additional electrical resistance.

22 Claims, 4 Drawing Sheets

U.S. PATENT DOCUMENTS

| | | |
|---|---|---|
| 5,542,928 A | 8/1996 | Evans et al. |
| 5,964,752 A | 10/1999 | Stone |
| 6,328,735 B1 | 12/2001 | Curley et al. |
| 7,156,868 B1 * | 1/2007 | Nashef et al. ............... 607/113 |

FOREIGN PATENT DOCUMENTS

| | | |
|---|---|---|
| WO | WO0029055 A1 | 5/2000 |
| WO | WO 02/069821 A1 | 9/2002 |
| WO | WO03070302 A1 | 8/2003 |

OTHER PUBLICATIONS

XP-002335290-E-Memoires de l' Academie Nationale de Chirurgie dated May 26, 2004.

* cited by examiner

IMPLANTABLE TUBE FOR INJECTION PARTICULARLY OF HEAT TRANSFER FLUID INTO ALL OR PART OF A HUMAN OR ANIMAL TISSUE

CROSS REFERENCE TO RELATED APPLICATIONS

This application is a national stage filing under section 371 of PCT International Application No. PCT/FR2006/050218, filed on Mar. 13, 2006, and published in French on Oct. 19, 2006 as WO2006/108974, and claims priority of French application No. 0550936, filed on Apr. 12, 2005, the entire disclosures of these applications are hereby incorporated herein by reference.

BACKGROUND ART

The invention relates to an implantable tube for injecting fluid into all or a part of a human or animal tissue. In the rest of the specification, the invention is described more particularly in relation to the injection of heat transfer fluid. However, the tube may also be used for injecting cold substances such as, for example, suspensions of magnetic nanoparticles or nanocapsules containing one or more active materials.

One of the methods for treating cancerous tumours consists in destroying all or part of the cancerous tissue by the targeted administration of heat or cold. This principle is known by the name "thermoablation" and is currently used in particular for treating liver metastases.

Many techniques based on the principle of heat-induced thermoablation are proposed today, such as laser, radio-frequency with needle, cryotherapy, which pertains to cold-induced thermoablation. However, these techniques have a number of drawbacks. In particular, the volume of the tumour treated remains limited (in practice 4 to 5 cm in diameter) and the operating time is relatively long, 20 to 30 minutes for radio-frequency and cryotherapy, even longer for laser treatment.

Document WO 00/29055 of the Applicant describes a heat-induced thermoablation technique whereby water or hydrogen peroxide is directly injected into the organism at a pressure of up to 3000 bar, at a temperature of 200 to 400° C. For this purpose, the hydrogen peroxide or water is heated in a metal coil incorporating an electrical resistor or a heat exchanger around which a platinum-iridium tube is wound. The alloy tube is connected to the diffusion means, which is in the form of a tube implanted directly into the tissue to be treated. This tube, referred to below as "microtube", has an outside diameter of between 100 and 250 µm, and an inside diameter of between 50 and 150 µm. It is made from a material suitable for withstanding the pressure of 3000 bar such as, for example, a platinum/iridium alloy, so that, when it is connected to the heating coil, it is suitable for injecting water or hydrogen peroxide in vaporized form. The temperature of the vaporized liquid, in contact with the tissue to be treated, decreases and the water returns to the liquid state inside the tumour.

In document WO 03/070302, the Applicant proposes a thermoablation method improved in that it provides for injecting the heat transfer fluid no longer continuously, but in pulsed form. In practice, the volume of liquid injected is very small, for example, between 0.2 and 1 ml, thereby avoiding the diffusion of heat outside the tumour. Furthermore, these volumes are injected at regular intervals of between 0.5 and 1 second, thus reducing the quantity of heat outside the zone to be treated, and thereby facilitating the handling of the tube by the surgeon.

In the two methods proposed, the heating system remains unchanged and essentially consists of a metal coil incorporating an electrical resistor and around which a stainless tube in which the heat transfer fluid flows is wound.

This heating system has a number of drawbacks.

Firstly, its position upstream of the installation demands a heating power commensurate with the length of the extension between the actual microtube and the heating system. Moreover, this system does not permit a sequencing, without any dead time, of the pulsed injection of hot products and cold products, because the coil cooling time is too long.

Document U.S. Pat. No. 5,542,928 describes a catheter designed for thermoablation conveying a fluid flowing externally at the distal end of the said tube via perforations. In practice, the liquid flowing in the tube is heated using a helical resistor arranged on the distal portion of the catheter and connected to an electric power supply. The catheter described in this document is designed to be introduced into the cavities for which it is unnecessary to have a small-diameter tube, the diameter being in fact between 2 and 10 mm. The presence of the resistor further increases the final diameter of the device designed to be introduced into the organism. While this document describes the idea of heating only the distal part of the tube, the size of the system proposed remains incompatible with a direct implantation into the tissues.

Document U.S. Pat. No. 6,328,735 B1 describes a thermoablation technique combining hot liquid injection and radio-frequency. More precisely, as above, the installation described comprises a tube whereof the distal end is provided with a resistor for heating the liquid arriving at the end of the tube. Here also, the tube diameter is advantageously 2 mm and the tube is surrounded by a coil having a resistance of 50Ω.

Document U.S. Pat. No. 5,964,752 describes an apparatus of the same type as above, for treating cartilages. Here also, the distal end of the tube is provided with a resistor, positioned this time inside the tube.

In all the cases, the heating systems proposed require a coil-shaped resistor generating a high inductance, incompatible with the current pulses like those used by the Applicant, because this would cause an excessively high impedance.

Document WO 02/069821 describes a tube in which vapour flows, for implanting in the organism. The vapour is generated directly in the tube in which the fluid flows by radio-frequency. More precisely, the tube has two electrodes connected to a radio-frequency generator, the liquid conveying the current between the two electrodes. In the proposed system, there is no differential heating and the tube is heated along its whole length. Moreover, the choice of the liquid to be injected is limited to conducting liquids. Finally, the current flow in the liquid is liable to affect the properties thereof.

In other words, the problem that the invention proposes to solve is to develop an installation of the type described for example in document WO 03/070302, in which the heat transfer fluid is heated to the vaporization temperature, exclusively in the distal part of the implantable microtube, the tube diameter being 10 to 20 times smaller than that of a catheter conventionally used for thermoablation.

A second problem that the invention proposes to solve is to develop a system in which the inductance is zero, making it usable with current pulses.

A third problem that the invention proposes to solve is to provide a single installation for injecting heat transfer fluid or cold fluid conveying nanocapsules or nanoparticles, according to the type of treatment involved.

The Applicant has developed a microtube connected to an electric power supply having a structure whereby it has a resistance of between 0.2 and 2Ω in its distal part and a resistance lower than 0.01Ω in its remaining part.

In other words, the electric power is concentrated in the distal part of the tube, thereby serving to reach temperatures of about 400° C.

The new system developed consists of a microtube for direct implantation into the tissues, the microtube being devoid of an additional electrical resistance and having a distal end capable of reaching high heating temperatures, the tube itself acting as a heating resistor. This tube is connected via an extension conveying the cold liquid, to the liquid storage and injection unit.

In other words, the invention relates to an implantable tube, for heating by conduction in particular a heat transfer fluid for injection into all or part of a human or animal tissue, the tube being provided with a wall having distal, median and proximal parts and comprising means for direct or indirect connection of the distal part to a fluid reservoir, characterized in that it is provided with two means for connection to the terminals of an electric power supply, for incoming and outgoing current in the wall, and in that it has a resistance less than 0.01Ω in its median and proximal parts, and a resistance of between 0.2 and 2Ω in its distal part, the median and proximal parts being connected electrically in series to the distal part, the tube having no additional electrical resistance, and having a practically zero inductance.

BRIEF SUMMARY OF THE INVENTION

The objective is therefore to have a microtube which can be implanted into the organism, and in which the heat transfer fluid is heated electrically and by conduction, only in the distal part of the microtube, that is, in the zone to be treated and not in the proximal and median parts, thereby serving to avoid heating the adjacent zones of tissue and facilitating the handling of the free proximal end of the tube by the surgeon.

To have a microtube with the abovementioned resistances, the wall of the implantable tube has, in an advantageous embodiment, from the centre to the periphery, in the cross section: a metal tube in which the fluid to be injected flows, with the exception of the distal part, a sheath for the incoming current, made from a conducting material joined to means for connection to one of the terminals of the electric power supply, with the exception of the free end of the distal part, an electrically insulating sheath, a sheath for the outgoing current, made from a conducting material joined to means for connection to the other terminal of the electric power supply.

Advantageously, the tube wall is provided with a biocompatible outer sheath for its implantation into the tissues.

According to a first feature, the metal tube has a resistivity of between 20 and 100 μΩ·cm and advantageously has a length shorter than 50 cm. In practice, the outside diameter of the tube is between 200 μm and 800 μm, advantageously equal to 250 μm, and the inside diameter is between 100 μm and 250 μm, advantageously equal to 150 μm.

In practice, the metal tube is made from a material of the platinum/iridium alloy, titanium, stainless steel, nickel-titanium alloy type, and more generally, any electrically conducting material capable of withstanding a pressure up to 3000 bar and a temperature of 400° C.

For the flow of incoming and outgoing current, the sheath comprises a copper electroplating between 20 μm and 50 μm thick.

With regard to the electrically insulating sheath, it consists advantageously of a titanium dioxide or alumina vacuum coating and, more generally, of any electrically insulating material withstanding a temperature of at least 400° C. The thickness of the sheath is between 200 nm and 400 nm.

Similarly, the outer sheath is preferably made from a gold electroplating about 1 μm thick.

The microtube of the invention can be used in two different ways.

Firstly, it can be implanted durably into the tissue for long-term treatment. In this situation, the distal part of the implantable tube is provided with perforations of between 50 μm and 150 μm, in size, advantageously equal to 70 μm, while its free end is blocked. In practice, the microtube is implanted using a split needle, the said needle being then removed, thereby leaving only the tube in the tissue.

The treatment can also be carried out occasionally. In such a situation, the microtube is withdrawn immediately after use. It is devoid of lateral perforations in its distal part and has a single open orifice, made at its free distal end. In this case, the microtube is used in combination with a needle whereof the walls are provided with perforations, the microtube being introduced into the body of the needle and the whole being implanted into the tissue to be treated.

The invention also relates to an installation particularly for injecting heat transfer fluid in pulsed conditions into all or part of a human or animal tissue, using the microtube described above. More precisely, such an installation contains:

a unit for storing the fluid;
a unit for injecting the said fluid;
the implantable tube described above;
an extension connecting the proximal end of the implantable tube to the injection unit.

In practice the injection unit is in the form of a chamber containing the substance to be injected, and in which a small diameter hydraulic cylinder, with a diameter of about 3 to 5 mm, is actuated by an electrical, pneumatic, piezoelectric or mechanical cylinder, having a larger diameter, about 50 to 80 mm, whereof the actuation and/or stroke and/or force and/or speed of travel are determined according to the desired rate, volume and pressure of injection of the substance into the extension by the hydraulic cylinder.

To avoid the backflow of substance into the extension after injecting the said substance, the injection unit contains two nonreturn valves. As already stated, the pressure at which the substance is injected depends on the speed of travel and the force of the cylinders, for example pneumatic, which are also programmed.

The injection unit is supplied with active ingredient by a storage unit. In practice, the liquid is fed to the injection unit in predefined volumes corresponding to the volume injected into the tumor. The reservoir is separated from the chamber by a nonreturn valve, preventing the backflow of liquid into the storage reservoir under the pressure of the piston. Once the cold pressurized liquid is propelled into the microtube, the microtube connected to an electric power supply is subjected to a low voltage current pulse concomitant with the cold water pulse, for heating the liquid to a temperature of 400° C. More precisely, the electric power supply is controlled synchronously with the injection unit.

In reality, the extension, in the form of an independent element, the prolongation of the metal tube, constitutes part of the implantable tube. This accordingly means that the extension has a resistivity of between 20 and 100 μΩ·cm. It has a length of between 2 and 3 m. Its outside diameter is between 200 μm and 800 μm, advantageously equal to 250 μm, and its inside diameter is between 100 μm and 250 μm, advantageously equal to 150 μm. In general, the larger the diameter, the larger the dead volume, which is unsatisfactory. As already stated, the metal tube is made from a material of the platinum/iridium alloy, titanium, stainless steel, nickel-titanium alloy type, and more generally, any electrically conducting material capable of withstanding a pressure up to 3000 bar and a temperature of 400° C. The extension is connected by any known means to the injection unit on one side, and to the proximal end of the microtube, on the other.

As already stated, one of the problems of the invention is to provide an installation thanks to which heat or cold can be injected according to the type of treatment required. This objective is achieved because it suffices to disconnect the electric power supply at the time of injection of the cold substance. Furthermore, the pulsed conditions, combined with the fact that only the distal part of the implantable tube is heated, serves to sequence the injection of heat and cold without pause, because the combination of extension and implantable tube, with the exception of the distal part, remains cold.

The cold active substance may have various forms, for example in the form of a suspension of nanocapsules, nanoparticles or microparticles. Also conceivable are all types of active substances, whether used for chemotherapy or for antibiotherapy, as well as anti-inflammatories and radioactive products for therapeutic use, and in a non-limiting manner.

In one advantageous embodiment, the active substance may be combined with magnetic ferrite nanoparticles between 100 and 1000 nanometers in size.

It follows that during the injection of the active substance through the tube, the energy communicated to the magnetic nanoparticles causes them to behave independently from one another, their mutual magnetic attraction becoming in fact negligible compared to their kinetic energy. On the other hand, after injection, that is in situ, the magnetic attraction favours the grouping of the nanoparticles in the form of clusters about 50 microns in size, in the zone of the tissue to be treated.

In the case of a radioactive active ingredient, the said radioactive active ingredient may have two different forms:
either it consists of radioactive isotopes grafted on the magnetic particles;
or it is included in the magnetic particle and consists of radioactive isotopes of the magnetic elements forming the magnetic particles.

Advantageously, the radioactive product may be an α, β and γ emitter for therapeutic purposes, preferably low energy, to obtain the most local possible irradiation. It may also be useful to include a γ emitter with energy between 100 and 150 kiloelectronvolts (keV) or a β+ emitter to visualise the location of the nanoparticles using a γ-camera. This also serves to facilitate the calculation of the irradiation dose.

As already stated, ferrite nanoparticles can be used as magnetic particles.

In this case, the stable product yielding the radioactive product by irradiation by neutrons or charged particles is incorporated during the fabrication of the ferrite nanoparticles, the components of the ferrite yielding very short-lived undesirable radioactive products after irradiation, and therefore, disappearing very quickly. In this way, only the radioactivity of the therapeutic radioelements selected persists.

In another embodiment, an active substance can be combined with liquid mercury (Hg) or a mercury amalgam in the form of nanoparticles. In fact, during the injection, the liquid mercury takes the form of microdrops whereof the kinetic energy is high owing to its high density. In situ, that is, in the organ, the high surface tension of mercury favours the grouping of the microdrops in larger beads, thereby fixing the active substance in the organ to be treated.

Moreover, mercury has a radioactive isotope (Hg 197) which is well adapted to therapy. In this way, the active ingredient Hg 197 is included in the mercury nanoparticles. Moreover, and as already stated, mercury produces amalgams with most metals, thereby serving to fix other metal radioactive products in the form of traces, the mercury remaining liquid.

BRIEF DESCRIPTION OF THE DRAWING FIGURES

The invention and its advantages will clearly appear from the exemplary embodiment described below, in conjunction with the figures appended hereto.

DETAILED DESCRIPTION

Figure 1:
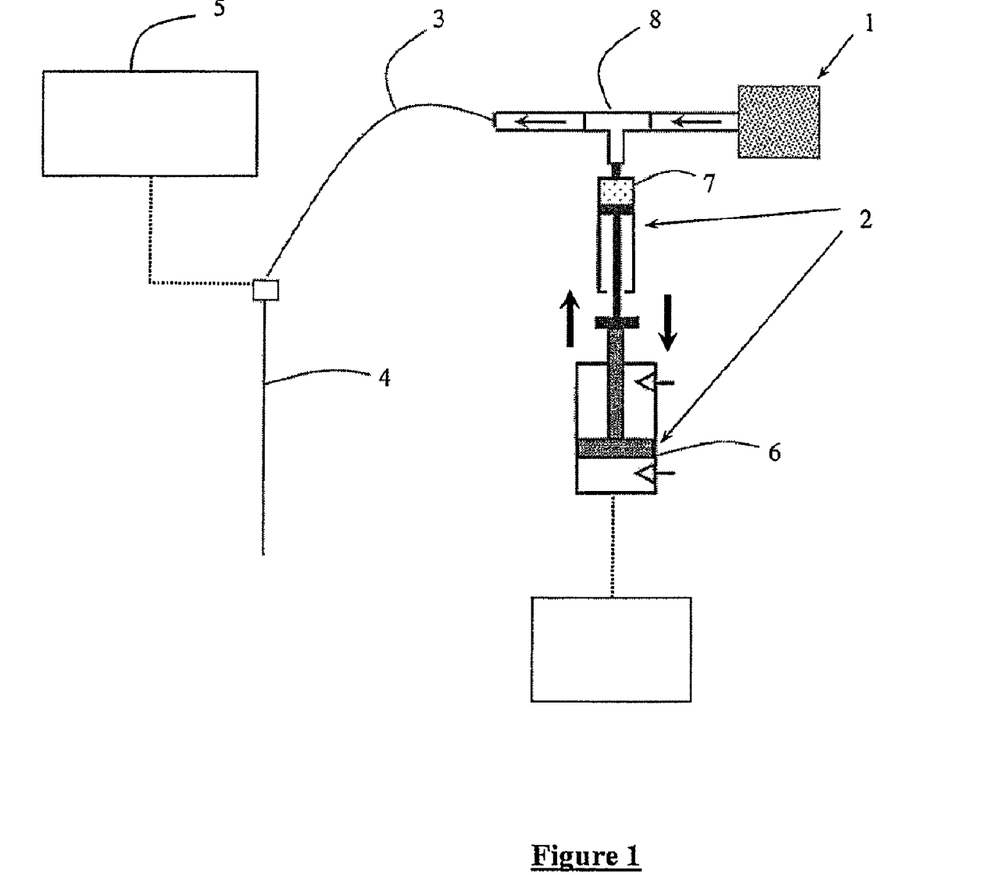
FIG. 1 is a schematic representation of the installation incorporating the implantable tube of the invention.

FIG. 1 schematically shows an installation for treating tissues by thermoablation, and tumours in particular. More precisely, this installation is designed to deliver water in vapour form, at a temperature of about 400° C., and in pulsed conditions, directly to the tumour.

The installation comprises five main elements, respectively a storage unit of liquid to be vaporised (1), an injection unit (2), an extension (3), the implantable tube of the invention (4) and a power generator (5) integrating a system for programming pulses, and for managing pressure and temperature and movement sensors.

The injection unit (2) comprises a large sized (6) pneumatic cylinder integral with a small sized hydraulic cylinder travelling in a chamber (7) where the liquid is pressurized, itself terminating in a tube (8) fed by the storage unit (1).

The stroke, force and speed of travel of the pneumatic cylinder are programmed according to the desired rate, volume and pressure of injection of the heat transfer liquid into the tube (8).

The extension (3) is in practice in the form of a tube about 2.5 m in length, whereof the outside diameter is 250 μm and the inside diameter is 150 μm. It is made from platinum/iridium, with a resistively of 25 μΩ·cm. As shown below, it constitutes the prolongation of the metal tube of the implantable tube. The extension is connected, at its proximal end, to the tube (8) and at its distal end, to the implantable tube (4) by a luer-lock or HPLC system.

Figure 2:
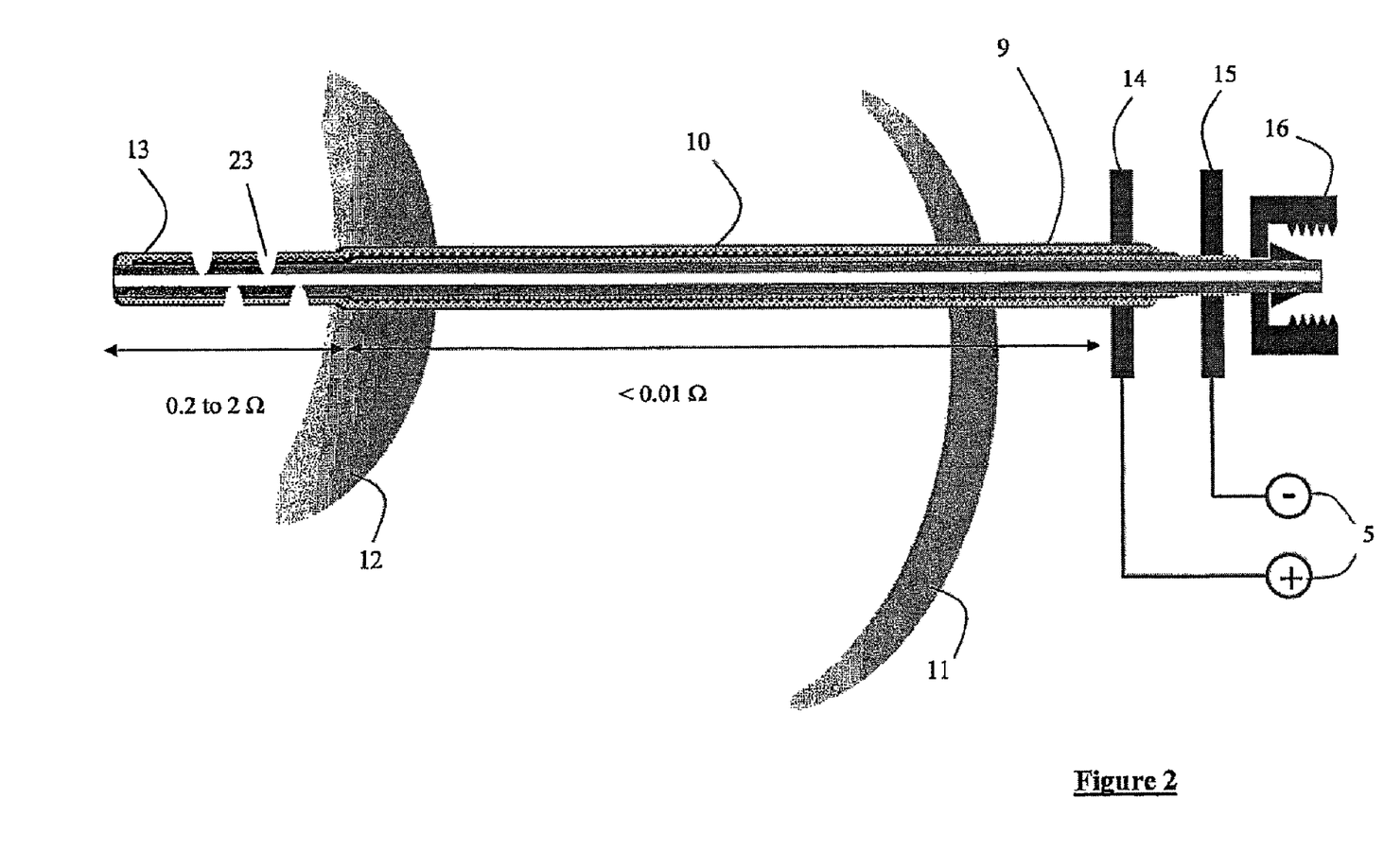
FIG. 2 is a representation of the implantable tube of the invention according to a first embodiment.

The microtube (4) is more particularly shown in FIG. 2. It is divided into three parts, respectively: a proximal part (9) corresponding in practice to the unimplanted part of the tube at the time of treatment;

a median part (10) corresponding in practice to the portion of the implanted tube located between the cutaneous plane (11) and the treatment zone (12), and a distal portion (13) located, at the time of treatment, in the zone to be treated.

The implantable microtube also has at its proximal end means (14, 15) for connection to the terminals of the electric power supply (5), and means (16) for connection to the distal end of the extension (3).

According to a feature, the median and proximal parts of the tube have a resistance lower than $0.01\Omega$, while the distal part has a resistance of between 0.2 and $2\Omega$, the median and proximal parts being electrically connected in series to the distal part. The difference in resistance of these zones serves to heat the liquid exclusively in the distal zone of the microtube, and not between the zone to be treated and the cutaneous plane, thereby avoiding the heating of the tissues not concerned by the treatment.

Figure 3:
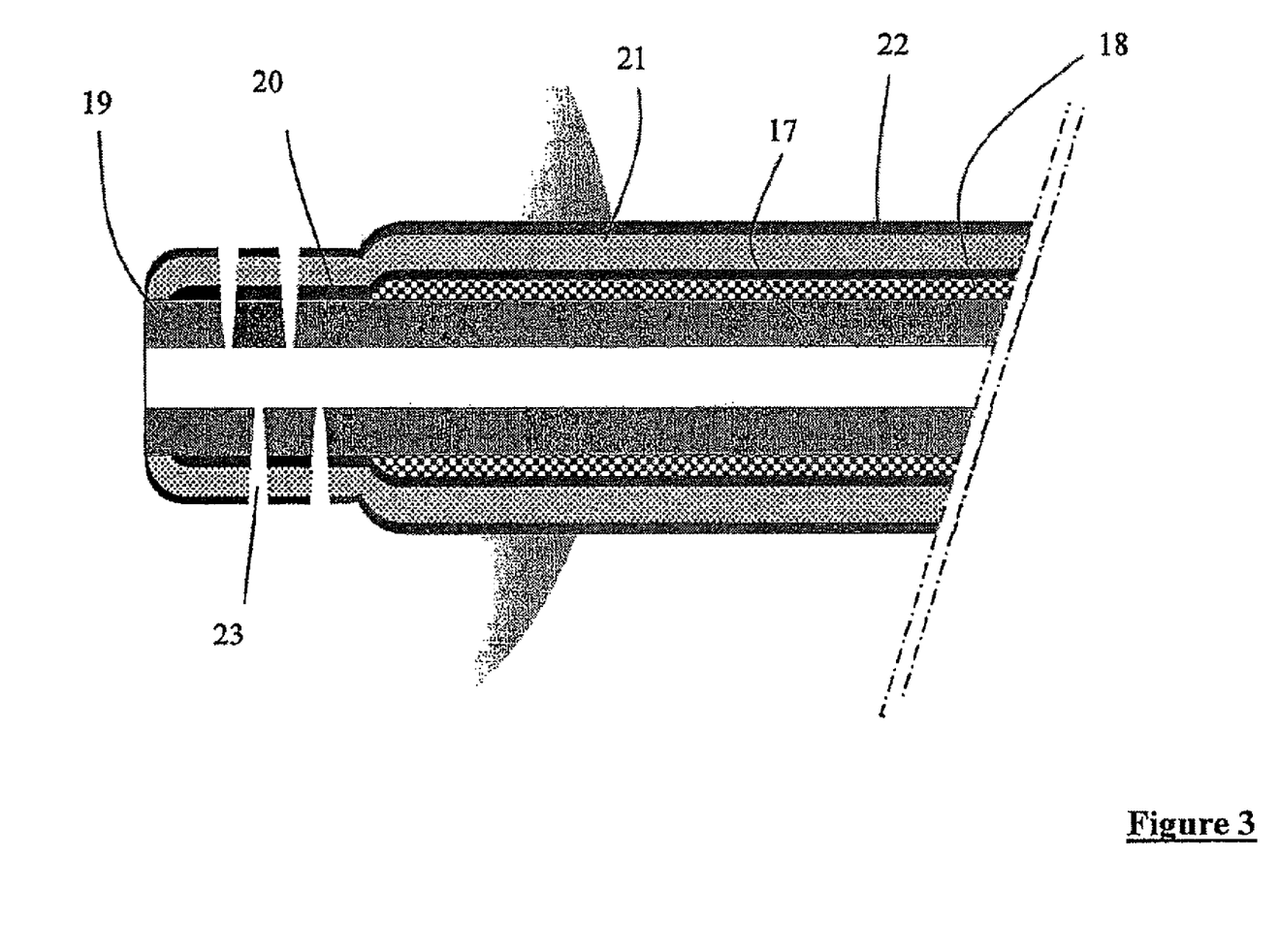
FIG. 3 is an enlargement of the distal part of the tube of FIG. 2.

FIG. 3 shows an enlargement of the microtube structure.

This tube consists from the centre to the periphery of a tube proper (17) made from platinum/iridium, having a variable length according to the depth of the zone to be treated. In practice, the size of the tube is less than 50 cm. The tube material has a resistivity of 25 $\mu\Omega\cdot$cm, and the tube has an inside diameter of 150 µm and an outside diameter of 250 µm.

In these median and proximal parts, the tube (17) is coated with a copper electroplating (18) 30 µm thick in contact at the proximal end with the connection (15) to the electric power supply (5) for incoming current flow. The distal part of the tube (17), with the exception of its distal end (19) is coated with an electrically insulating sheath (20) made from a titanium dioxide vacuum coating, the sheath covering the copper electroplating for the incoming current flow to the median and proximal parts of the tube.

On the insulating sheath (20), and in contact with the distal end (19) of the tube (17), the implantable tube of the invention has a copper electroplating (21) for outgoing current flow, which is in contact with the second connector (14) connected to the electric power supply (5). The outermost sheath is a biocompatible sheath (22) having the form of a gold electroplating.

In practice, the cold liquid arrives at the proximal end of the tube in the form of a pulse and is slightly heated under the action of the synchronous current pulses. This heating remains low because of the choice of the resistance, lower than $0.01\Omega$. At the distal part, the current flows directly into the wall of the tube (17) to flow to the distal end (19) via the sheath (20).

The implantable tube of the invention may have two distinct conformations.

In the first conformation shown in FIG. 2, the tube is blocked at its free distal end (19) and, in the distal part, has perforations (23) 70 microns in size.

This type of microtube is used for long-term treatments, requiring the maintenance of the microtube in the organism until the end of the said treatment. The tube is inserted via a laterally split puncture needle serving as a guide. Once the assembly is introduced into the tissue to be treated, the needle is released from the tube, and then removed.

Figure 4:
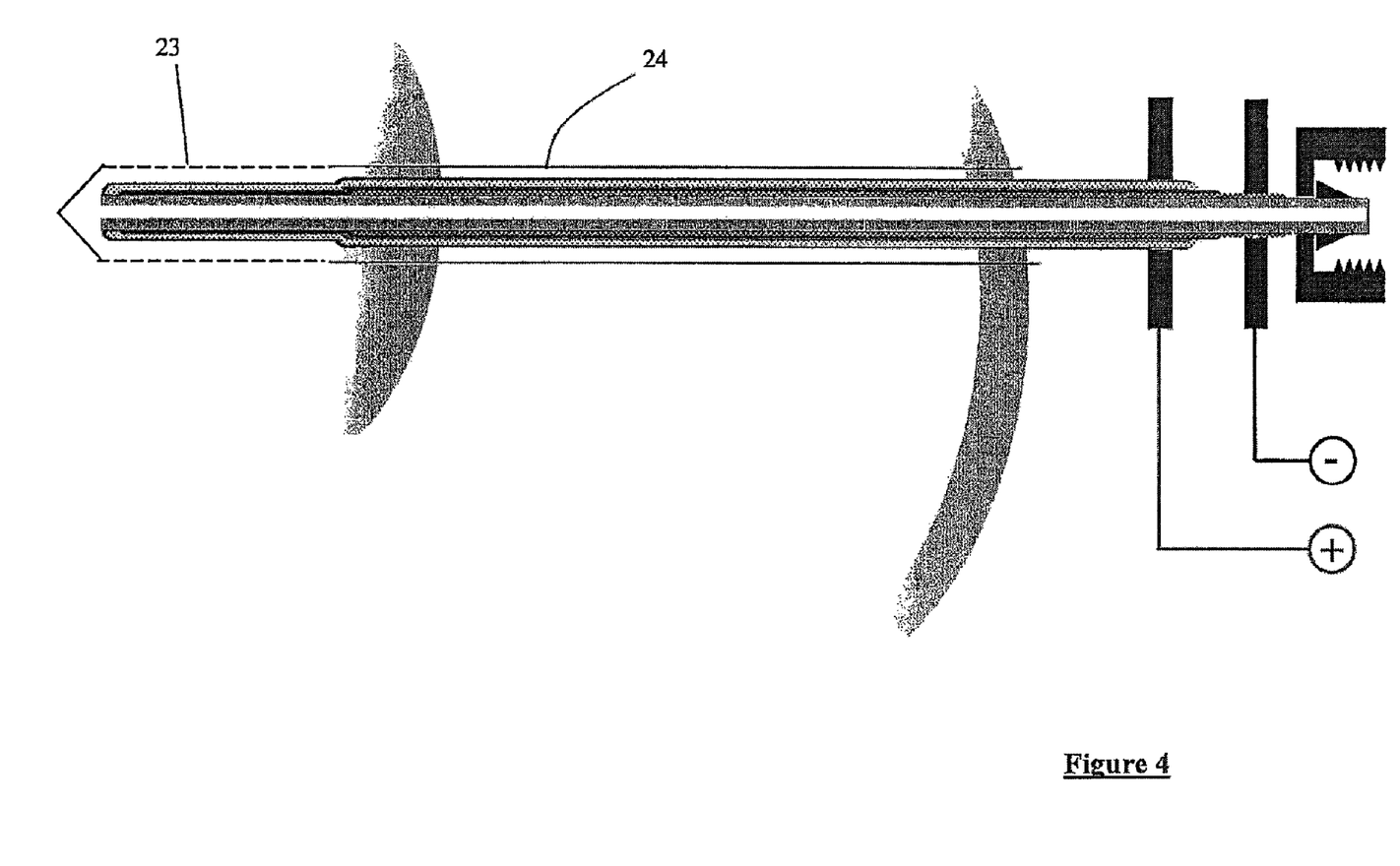
FIG. 4 is a second embodiment of the implantable tube of the invention.

In a second embodiment, the implantable tube of the invention is used for occasional treatments. In this situation, the tube is systematically removed after each introduction. In this case, the system shown in FIG. 4 is implemented.

In practice, the microtube is identical to the one shown in FIG. 2, except that it has an open free distal end, and is devoid of perforations. The perforations (23) are, on the other hand, provided in the puncture needle (24) introduced into the tissue to be treated.

Obviously, these perforated puncture needles can also be used with microtubes which are themselves perforated, as shown in FIG. 3.

The use of the system will now be described in greater detail.

The operator determines the volume of substance to be injected according to the size of the tumour. From his experience, in the case of thermoablation, the Applicant has found that it is generally necessary to inject a volume of liquid representing 5 to 10% of the volume of the tumour to be treated to obtain satisfactory necrosis (at 400° C.). The operator then determines the volume of each injection and infers the number of pulses necessary to succeed in delivering the total volume of liquid. The actuation, stroke, force and speed of the pneumatic cylinder are then programmed for injecting N times the volume of liquid at regular intervals, in practice between 0.05 and 1 ml, by pulses with durations between 1 and 2 seconds at a pressure of 2 200 bar.

The handling then begins by injecting the first volume of cold water into the extension. At the same time as the injection, a voltage of 6 to 20 volts is applied to the terminals (14) and (15) of the tube. The very low resistance of the proximal and median parts of the tube serves to limit the heating of the fluid, the temperature being about 45° C. in practice. In the distal zone, which has a resistance of $2\Omega$, the temperature reaches 400° C. in 4 to 5 seconds, for a pressure of 2 200 bar. At the next cold water pulse, the water that has vaporised escapes via the perforations of the tube and via its distal end, and the vapour condenses to hot water close to the boiling point by releasing heat into the tumour.

The invention and the advantages thereof clearly appear from the above description. Particularly noteworthy is the absence of an independent heating unit and the advantage of being able to heat a certain volume of water directly in the zone to the treated.

The invention claimed is:

1. Implantable tube for heating by conduction a heat transfer fluid for injection into all or part of a human or animal tissue, the tube being provided with a wall having a distal part in contact with a zone to be treated, a median part and a proximal part, the distal part and the median part being adapted for tissue implantation, and comprising means for directly or indirectly connecting the proximal part to a fluid reservoir, further comprising two means for connection of the wall to terminals of an electric power supply, for incoming and outgoing current in the wall, and the tube having a resistance less than $0.01\Omega$ in the median part and the proximal part, and a resistance of between 0.2 and $2\Omega$ in the distal part, the median part and the proximal part being connected electrically in series to the distal part, wherein the distal part produces substantially all of the heating by conduction of the heat transfer fluid in the tube.

2. Tube according to claim 1, wherein the wall has, in a cross section from a center to a periphery:
   a metal tube in which the fluid to be injected flows,
   with the exception of the distal part, a sheath for the incoming current, made from a conducting material joined to means for connection to one of the terminals of the electric power supply,
   with the exception of a free end of the distal part, an electrically insulating sheath, and
   a sheath for the outgoing current, made from a conducting material joined to means for connection to an other terminal of the electric power supply.

3. Tube according to claim 2, wherein the metal tube has a resistivity of between 20 and 100 μΩ·cm.

4. Tube according to claim 3, wherein the metal tube is made from a platinum/iridium or nickel-titanium alloy, or from titanium or stainless steel.

5. Tube according to claim 2, wherein the metal tube has the following characteristics:
   length shorter than 50 cm,
   outside diameter between 200 μm and 800 μm, and
   inside diameter between 100 μm and 250 μm.

6. Tube according to claim 5, wherein the outside diameter is equal to 250 μm, and the inside diameter is equal to 150 μm.

7. Tube according to claim 2, wherein the sheath for the incoming and outgoing current flow comprises a copper electroplating between 20 μm and 50 μm thick.

8. Tube according to claim 2, wherein the electrically insulating sheath comprises a titanium dioxide vacuum coating between 200 nm and 400 nm thick.

9. Tube according to claim 2, wherein the metal tube has an outside diameter of between 200 μm and 800 μm, an inside diameter of between 100 μm and 250 μm, and withstands a pressure up to 300 bar and a temperature of 400° C.

10. Tube according to claim 1, wherein the tube comprises a microtube having an outside diameter of between 100 μm and 250 μm, and an inside diameter of between 50 μm and 150 μm.

11. Tube according to claim 1, wherein the wall is provided with a biocompatible outer sheath.

12. Tube according to claim 11, wherein the outer sheath is made from a gold electroplating about 1 μm thick.

13. Tube according to claim 1, wherein the distal part is provided with vapor escape perforations and has a free end that is blocked.

14. Tube according to claim 13, wherein the perforations have a size of between 50 μm and 150 μm.

15. Tube according to claim 1, wherein a free end of the distal part is provided with an open orifice.

16. Installation for injecting a heat transfer fluid in pulsed conditions, into all or part of a human or animal tissue, comprising:
   a unit for storing the fluid;
   an injection unit for injecting said fluid;
   the implantable tube according to claim 1; and
   an extension connecting the proximal part of the implantable tube to the injection unit.

17. Installation according to claim 16, wherein the injection unit comprises a chamber containing a substance to be injected, and further comprising a hydraulic cylinder actuated by an electrical, pneumatic, piezoelectric or mechanical cylinder whereof an actuation and/or stroke and/or force and/or speed of travel are determined according to a desired rate, volume and pressure of injection of the substance in the extension by the hydraulic cylinder.

18. Installation according to claim 16, wherein the implantable tube has substantially zero inductance.

19. Installation according to claim 16, wherein the fluid comprises at least one of cold water and a cold active substance.

20. Tube according to claim 1, wherein the heat transfer fluid is heated to a vaporization temperature by the distal part.

21. Tube according to claim 1, devoid of any additional electrical resistance.

22. Tube according to claim 1, having a substantially zero inductance.

* * * * *